United States Patent [19]

Le Baut et al.

[11] Patent Number: 5,315,017

[45] Date of Patent: May 24, 1994

[54] BENZOPYRAN

[75] Inventors: Guillaume Le Baut, Saint Sebastien Sur Loire; Jean-Paul Babingui, Nantes; Jacqueline Courant, Nantes; Jean-Michel Robert, Nantes; Pierre Renard, Versailles; Daniel-Henri Caignard, Paris; Jean-Francois R. de la Faverie, Chesnay; Gérard Adam, Le Mesnil Le Roi, all of France

[73] Assignee: Adir Et Compagnie, Courbevoie, France

[21] Appl. No.: 876,763

[22] Filed: May 1, 1992

[30] Foreign Application Priority Data

May 3, 1991 [FR] France .................. 91 05418

[51] Int. Cl.$^5$ ............... A61K 31/35; A61K 31/44; A61K 31/47; C07D 31/04; C07D 405/12
[52] U.S. Cl. ................... 549/408; 546/146; 546/159; 546/256
[58] Field of Search ............ 546/159, 256, 146; 549/408; 514/456, 337, 314, 307

[56] References Cited

U.S. PATENT DOCUMENTS 4,816,484  3/1989  Toyoshima et al. .......... 546/169
5,017,604  5/1991  Belliotti et al. ............ 574/482

FOREIGN PATENT DOCUMENTS

88/01212  4/1988  PCT Int'l Appl. .

OTHER PUBLICATIONS

Davies, Kelvin J. A., "Oxidative Damage and Repair, Chemical, Biological and Medical Aspects", Pergamon Press, page xxi, 1990.
Halliwell, Barry, "Drug Antioxidant Effects-A Basis for Drug Selection", USA in Drugs 42 (4), 569-605 (1991).
Slater, T., and Jacob, H. S., "New Developments In Free Radical Research", International Conference held Oct. 15-16, 1990.
Goodman and Gilman, "The Pharmacological Basis of Therapeutics", 8th Edition, Pergamon Press, p. 603 (1983).
Goodman and Gilman, "The Pharmacological Basis of Therapeutics", 8th Edition, Pergamon Press, pp. 600, 610 (1983).

Primary Examiner—David B. Springer
Attorney, Agent, or Firm—Gordon W. Hueschen

[57] ABSTRACT

A compound selected from the group consisting of those of formula I

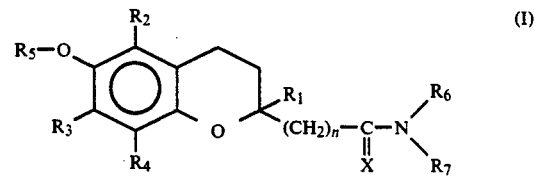

in which $R_1$, $R_2$, $R_3$, $R_4$, $R_5$, $R_6$, $R_7$, X and n are defined in the description, an optical isomer thereof, and an addition salt thereof with a pharmaceutically-acceptable base or acid.

Medicinal product which is useful in treating or in preventing a disorder due to or linked to the phenomena of peroxidation and to the disturbance of the eicosanoid biosynthesis.

21 Claims, No Drawings

BENZOPYRAN

The present invention relates to new benzopyran compounds.

Numerous benzopyran compounds are known, especially tocopherols which are vitamin E compounds possessing antioxidant properties in particular. Numerous tocopherol compounds have been prepared which result from modification of the side chain of alkanoic nature without increasing the antioxidant activity. Other benzopyran compounds such as (6-hydroxy-2,5,7,8-tetramethylchroman-2-yl)carboxylic acid possess a good antioxidant activity, but solely for industrial use, having failed to gain therapeutic applications.

More recently, Patent Application WO 88/08424 described other chroman-2-carboxylic acid compounds and more generally (chroman-2-yl)alkylcarboxylic acid compounds possessing advantageous antioxidant properties.

The Applicant has now discovered new benzopyran compounds, and more particularly (benzopyran-2-yl)carboxylic acid or (chroman-2-yl)carboxylic acid compounds possessing an antioxidant activity which is substantially higher than that of the compounds of Application WO 88/08424 which constitute the most related prior art.

More specifically, the invention relates to new benzopyran compounds of the general formula (I):

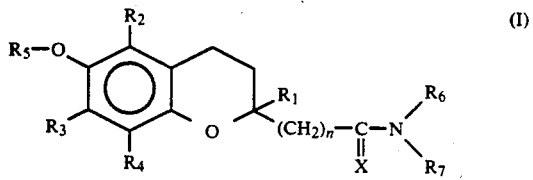

in which:

n represents an integer equal to 0 or 1,

X represents an oxygen atom or 2 hydrogen atoms, $R_1$, $R_2$, $R_3$ and $R_4$, which are identical or different, each represent independently of one another a hydrogen atom or a lower alkyl radical $R_a$-, where Ra represents a linear or branched alkyl group with 1 to 8 carbon atoms, $R_5$ represents:
a hydrogen atom,
a lower alkyl group $R_a$-,
a lower acyl group Ra—CO—,
an alkoxyalkyl group of the form $R_a$—O—$R_b$—,
an alkoxycarbonyl group of the form $R_a$—O—CO—,
an alkoxycarbonylalkyl group of the form $R_a$—O—CO—$R_b$—,
a carboxyalkyl group of the form HOOC—$R_a$—,
where $R_a$ and $R_b$, which are identical or different, each represent independently of one another, a linear or branched alkyl radical comprising 1 to 8 carbon atoms, $R_6$ and $R_7$ - either: form together with the nitrogen atom carrying them an E group or a substituted E group, with E representing a heterocyclic spiro group with 8 to 12 members including, in its carbon skeleton, 1 to 4 hetero atoms chosen from nitrogen, sulfur, and oxygen,
—or:
which are identical or different, each represent independently of one another:

a hydrogen atom,
a lower alkyl group Ra- or a substituted lower alkyl group $R_a$-,
a lower alkenyl group or a substituted lower alkenyl group where the alkenyl group represents an unsaturated, linear or branched hydrocarbon comprising 2 to 8 carbon atoms,
a group A—(CH$_2$)$_m$— or a substituted group A—(CH$_2$)$_m$—, where m is an integer equal to 0, 1 or 2 and A represents a cycloalkyl group comprising p carbon atoms with p being an integer from 3 to 7, it being understood that if p is 3 or 4 then m may be 0, 1 or 2 and if p is 5, 6 or 7 then m can only be 1 or 2,
an alkoxyalkyl group of the form $R_a$—O—$R_b$— or a substituted alkoxyalkyl group of the form $R_a$—O—$R_b$—, where Ra and $R_b$, which are identical or different, represent a linear or branched lower alkyl radical with 1 to 8 carbon atoms,
an alkoxycarbonylalkyl group of the form $R_a$—O—CO—$R_b$— $R_b$— or a substituted alkoxycarbonylalkyl group of the form Ra—O—CO—$R_b$—, with $R_a$ and $R_b$ as defined above,
a group B—(CH$_2$)$_q$— or a substituted group B—(CH$_2$)$_q$—, where q is an integer equal to 0, 1, 2 or 3 and B represents a radical selected from naphthyl, 1,3-dioxane, pyran, and benzopyran,
a group E-(CH$_2$)$_q$— d group E—(CH$_2$)$_q$—, with q and E as defined above,
a group phenyl-(CH$_2$)$_q$— or a substituted group phenyl-(CH$_2$)$_q$—, with q as defined above,
a group heteroaryl-(CH$_2$)$_q$— or a substituted group heteroaryl-(CH$_2$)$_q$—, with q as defined above and where the heteroaryl is selected from:
furan, quinoline, isoquinoline, pyridine, thiophene, thiazole, isothiazole, oxazole, isoxazole, naphthyridine, benzofuran, β-carboline, and γ-carboline, one of the following radicals $D_1$ to $D_9$ or one of the following substituted radicals $D_1$ to $D_9$:

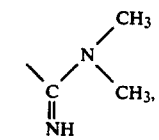

D$_1$

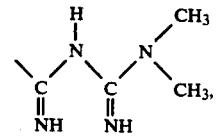

D$_2$

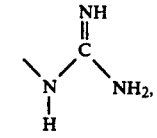

D$_3$

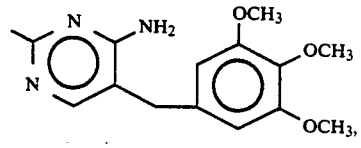

D$_4$

-continued

D5 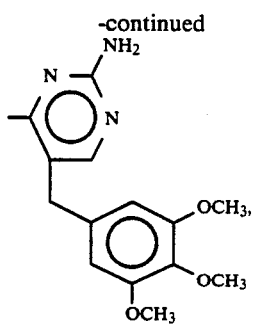

D6 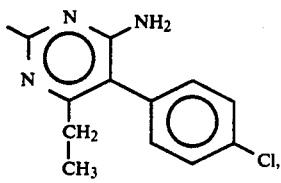

D7 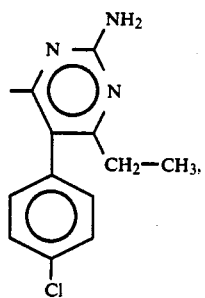

D8 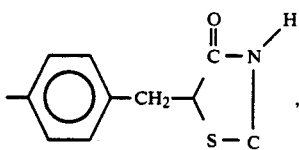

D9 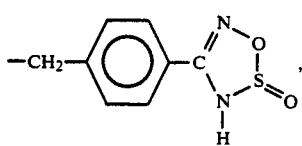

it being understood that when one of the substituents $R_6$ or $R_7$ represents a hydrogen atom, a lower alkyl group comprising not more than 3 carbon atoms, an unsubstituted group phenyl-$(CH_2)_{q'}$—, a group phenyl-$(CH_2)_{q'}$— which is substituted by 1 or 2 radicals, an unsubstituted group pyridinyl-$(CH_2)_q$—, or a group pyridinyl-$(CH_2)_q$— which is substituted by 1 or 2 radicals, with q as defined above and q' being an integer equal to 1, 2 or 3, then at least one of the following 2 conditions is true:

either the other substituent, $R_6$ or $R_7$ as appropriate, does not represent: a hydrogen atom, a lower alkyl group comprising not more than 3 carbon atoms, an unsubstituted group phenyl-$(CH_2)_{q'}$—, a group phenyl-$(CH_2)_{q'}$— which is substituted by 1 or 2 radicals, an unsubstituted group pyridinyl-$(CH_2)_q$—, a group pyridinyl-$(CH_2)_q$— which is substituted by 1 or 2 radicals, with q and q' as defined above, or the substituent $R_5$ does not represent a hydrogen atom, a lower alkyl group comprising not more than 4 carbon atoms, or a lower acyl group $R'_5$—CO—, with $R'_5$ representing a lower alkyl radical comprising not more than 4 carbon atoms, it being understood that for this description of the general formula (I), the term "substituted" concerning the groups as defined above: lower alkyl $R_a$—, lower alkenyl, A—$(CH_2)_m$—, alkoxyalkyl $R_a$—O—$R_b$—, alkoxycarbonylalkyl $R_a$—O—CO—$R_b$—, B—$(CH_2)_q$—, E-$(CH_2)_q$—, phenyl-$(CH_2)_q$—, phenyl-$(CH_2)_{q'}$—, heteroaryl-$(CH_2)_q$—; $D_1$ to $D_9$, means, when it is not specified, that these groups may be substituted by one or more radicals, which may be identical or different, and each one of which may represent independently of one another:

a lower alkyl group $R_c$—,
a lower alkoxy $R_c$—O—,
a lower acyl $R_c$—CO—,
a trifluoromethyl,
a carboxyl,
a hydroxyl,
an amino,
an amino, which is substituted by 1 or 2 lower alkyl groups $R_c$—,
a nitro,
an oxo,
a phenyl,
a lower alkylthio $R_c$—S—,
a thiol,
or a halogen atom, where $R_c$ represents a linear or branched alkyl group with 1 to 6 carbon atoms, their optical isomers, as well as, where appropriate, their addition salts with a Pharmaceutically acceptable acid or base.

Among the pharmaceutically acceptable acids or bases which may be used to salify the compounds of the invention, hydrochloric, hydrobromic, sulfuric, nitric, oxalic, malic, maleic, succinic, tartaric, methanesulfonic, camphoric and camphosulfonic acids, sodium hydroxide, potassium hydroxide, triethylamine, diethylamine, ethanolamine, arginine, lysine and diethanolamine, may be mentioned by way of examples with no limitation being implied.

The compounds of formula (I) are easily obtained by a process wherein a compound of formula (II) is used as starting material:

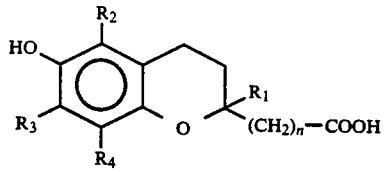

with $R_1$, $R_2$, $R_3$, $R_4$ and n having the same meaning as in the general formula (I), which compound may be etherified or esterified, in an anhydrous basic medium, with a compound $R_5''$-Hal or $R_5''$—O—$R_5$ of where Hal represents a halogen atom and where $R_5''$ represents a lower alkyl group Ra—, a lower acyl group $R_a$—CO—, an alkoxyalkyl group of the form $R_a$—O—$R_b$—, an alkoxycarbonyl group of the form Ra—O—CO—, an alkoxycarbonylalkyl group of the form $R_a$—O—CO—$R_b$—, a carboxyalkyl group of the form HOOC—$R_a$—, formulae in which Ra and Rb, which are identical or different, each represent independently of one another a linear or branched lower alkyl group comprising 1 to 8 carbon atoms, to give a compound of formula (III):

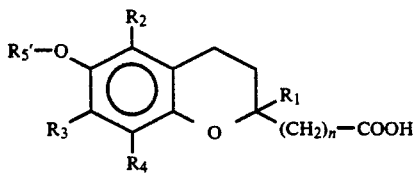

with $R_1$, $R_2$, $R_3$, $R_4$, n and $R_5''$ as defined above, which compound is converted to its chloride by the action of a halogenating agent, and then treated, in an appropriate solvent, in the presence of an alkaline agent, with an amine of formula (IV):

with $R_6$ and $R_7$ having the same meaning as in formula (I) to give a compound of formula ($I_a$):

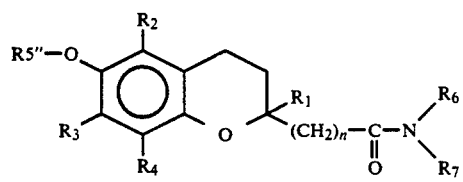

with $R_1$, $R_2$, $R_3$, $R_4$, $R_6$, $R_7$, n and $R_5''$ as defined above, which is a specific example of the compounds of formula (I) for which $R_5$ represents a group $R_5''$ and X represents an oxygen atom, which compound may then be:
either reduced by the action of a mixed hydride of an alkali metal to a compound of formula ($I_b$):

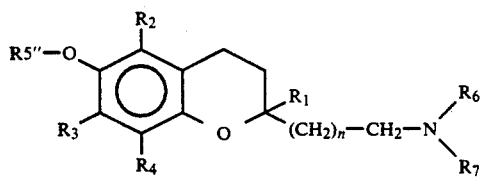

with $R_1$, $R_2$, $R_3$, $R_4$, $R_6$, $R_7$, n and $R_5''$ as defined above, which is a specific example of the compounds of formula (I) for which $R_5$ represents a group $R_5''$ and X represents two hydrogen or saponified by the action of an alkali or atoms, alkaline-earth metal hydroxide to a compound of formula ($I_c$):

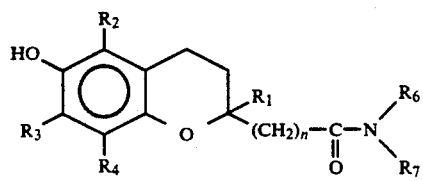

with $R_1$, $R_2$, $R_3$, $R_4$, $R_6$, $R_7$, and n as defined above, which is a specific example of the compounds of formula (I) for which $R_5$ represents a hydrogen atom and X represents an oxygen atom, which compound ($I_c$) may then be:

either reduced by the action of a mixed hydride of an alkali metal to a compound of formula ($I_d$):

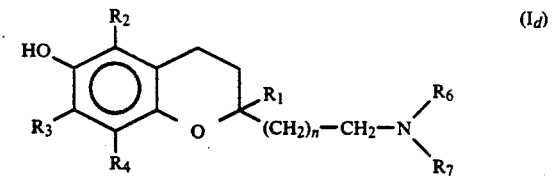

with $R_1$, $R_2$, $R_3$, $R_4$, $R_6$, $R_7$, and n as defined above, which is a specific example of the compounds of formula (I) for which $R_5$ represents a hydrogen atom and X represents 2 hydrogen atoms, or etherified or esterified so as to give, if desired, a group $R_5$ which is different from that present in the formula ($I_b$), by the action of a compound of formula $R_5'''$—O—$R_5'''$ or $R_5'''$—Hal, where Hal represents a halogen atom and $R_5'''$ represents a lower acyl group $R_a$—CO—, an alkoxyalkyl group of the form $R_a$—O—$R_b$—, an alkoxycarbonylalkyl group of the form $R_a$—O—CO—$R_b$—, or a carboxyalkyl group of the form HOOC—$R_a$—, with $R_a$ and $R_b$ as defined above, to give a compound of formula ($I_e$):

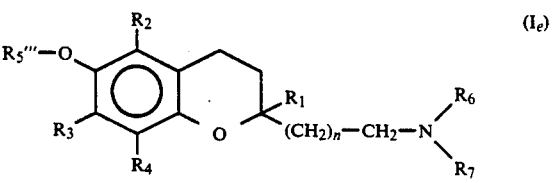

with $R_1$, $R_2$, $R_3$, $R_4$, $R_6$, $R_7$, n, and $R_5'''$ as defined above, which is a specific example of the compounds of formula (I) for which $R_5$ represents a group $R_5'''$ and X represents 2 hydrogen atoms.

The compounds of formula ($I_a$), ($I_b$), ($I_c$), ($I_d$), and ($I_e$) form the set of compounds of formula (I) which may be purified and/or separated, if desired, to give their optical isomers.

These compounds of formula (I) may also be converted, where appropriate, to their addition salts with a pharmaceutically acceptable base or acid.

Compared to the prior art compounds, these compounds of the present invention possess, surprisingly, very high antioxidant properties. Pharmacological studies have shown in particular that these compounds possess remarkable protective activity in relation to cellular lipid and low density lipoprotein (LDL) peroxidation processes.

These activities, are for some compounds of the invention, 100 times higher than that of the most related prior art compound, that is to say Example 102 of Application WO 88/08424.

Moreover, the compounds of the present invention possess the characteristic of having a potent inhibitory effect on the biosynthesis of eicosanoids, which compounds are derived from peroxidized compounds which are potential generators of free radicals, an inhibitory effect which the most related prior art compound does not possess.

Compounds of the invention may therefore be expected which possess both lipid peroxidation and eicosanoid biosynthesis inhibiting properties, an action which is particularly novel and beneficial in disorders involving not only membrane lipid peroxidation but a disorder of eicosanoid synthesis as well.

The compounds of the present invention may thus be used in the treatment or the prevention of disorders due to or linked to such phenomena of peroxidation and to such disturbance of the eicosanoid biosynthesis, and especially central or peripheral ischemic disorders, inflammatory diseases, rheumatoid arthritis, metabolic diseases, atheroma, arteriosclerosis, respiratory diseases, asthma, emphysema, diseases of immunological origin, lupus erythematosus, allergic reactions, certain cancers, cerebral or skin aging and in the prevention and treatment of damage due to surgical traumas such as organ reperfusion.

The subject of the present invention is also pharmaceutical compositions containing one of the compounds of formula I, or one of their addition salts with a pharmaceutically acceptable acid or base, alone or in combination with one or more inert, non-toxic excipients.

Among the pharmaceutical compositions according to the invention, there may be mentioned more particularly, by way of examples and with no limitation being implied, those which are suitable for oral, parenteral, nasal, rectal, perlingual, ocular or pulmonary administration, and especially preparations for injection, aerosols, eye or nasal drops, simple, coated or sugared tablets, gelatin capsules, capsules, creams, pomades and skin gels.

The required dosage varies according to the age and the weight of the patient, the route of administration, the nature of the disorder and the treatments which may be associated, and ranges between 0.5 mg and 2 grams per 24 hours.

The following examples illustrate the invention and do not imply any limitation.

The starting material is described in the literature or can easily be obtained by a person skilled in the art.

The infrared spectra are produced in potassium bromide pellets containing about 1% of the product to be analyzed.

EXAMPLE 1

N-Isobutyl-N-(4,6-dimethylpyridin-2-yl)-(6-acetoxy-3,4-dihydro-2,5,7,8-tetramethyl-2H[1]-benzopyran-2-yl)carboxamide STAGE A :
(6-Acetoxy-3,4-dihydro-2,5,7,8-tetramethyl-2H[1]-benzopyran-2-yl)carboxylic acid 50 grams (0.2 mole) of (6-hydroxy-3,4-dihydro-2,5,7,8-tetramethyl-2H[1]-benzopyran-2-yl)carboxylic acid are dissolved in 150 cm$^3$ of anhydrous pyridine. 9.4 cm$^3$ (0.1 mole) of acetic anhydride are added dropwise under a nitrogen stream. The mixture is stirred for 2 hours at a temperature of 30° C. After cooling, the mixture is poured into ice, the expected product extracted with ethyl ether, the organic phase washed with a 0.2 N solution of hydrochloric acid and then with water until neutral. After evaporation of the solvent, an oily mass is obtained which crystallizes after trituration in diisopropyl ether.

STAGE B :
N-Isobutyl-N-(4,6-dimethylpyridin-2-yl)-(6-acetoxy-3,4-dihydro-2,5,7,8-tetramethyl-2H[1]-benzopyran-2-yl)carboxamide 3.21 grams (11.21 mmol) of the compound from stage A of Example 1 above, are dissolved in 40 cm$^3$ of anhydrous benzene and 1.2 cm$^3$ of thionyl chloride are added. The mixture is refluxed for 3 hours and allowed to cool. The solvent is expelled under vacuum by removing excess thionyl chloride. The acid chloride thus obtained is dissolved in 25 cm$^3$ of dichloroethane.

2 grams (11.21 mmol) of N-(4,6-dimethylpyridin-2-yl)isobutylamine and 4.7 cm$^3$ of triethylamine are dissolved, in another vessel, in 25 cm$^3$ of dichloroethane, the above acid chloride solution is then poured dropwise into this mixture, refluxed for 3 hours and the solvent evaporated under vacuum. The residue obtained is taken up in 30 cm$^3$ of water, neutralized with a solution of sodium bicarbonate, extracted with dichloromethane, the organic phase washed and then dried. After removing the solvent, the product is purified using conventional chromatographic or crystallographic separation techniques.

The title product is obtained:
Yield: 55%
Melting point: 90°-92° C.
Infrared spectra characteristics:
$\nu$C=O (ester): 1750 cm$^{-1}$
$\nu$C=O (amide): 1650 cm$^{-1}$
$\nu$C=C, C=N: 1600, 1550 cm$^{-1}$

EXAMPLE 2

N-Isobutyl-N-(4,6-dimethylpyridin-2-yl)-(6-hydroxy-3,4-dihydro-2,5,7,8-tetramethyl-2H[1]-benzopyran-2-yl)carboxamide 2.6 grams (5.74 mmol) of the compound from Example 1 are dissolved in 80 cm$^3$ of 60% ethanol and 14 cm$^3$ of 2.5 N sodium hydroxide are added. The mixture is stirred for 3 hours and then diluted with water and acidified with acetic acid. The product is extracted with dichloromethane, the organic phase washed with water, dried over anhydrous sodium sulfate and the solvent evaporated. The oil obtained is taken up in 15 cm$^3$ of isopropyl ether and the product is isolated using conventional chromatographic or crystallographic separation techniques.

The title product is obtained:
Yield: 96%
Melting point: 159°-160° C.
Infrared spectra characteristics:
$\nu$C=O: 1360 cm$^{-1}$
$\nu$C=O: 3600-3200 cm$^{-1}$
$\nu$C=C, C=N: 1605, 1560 cm$^{-1}$

EXAMPLE 3

N-(2,4,6-Trimethylphenyl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 2,4,6-trimethylaniline:
Yield: 73.7%
Melting point: 148°-149° C.
Infrared spectra characteristics:
$\nu$C=O (ester): 1750 cm$^{-1}$
$\nu$C=O (amide): 1680 cm$^{-1}$
$\nu$NH: 3400 cm$^{-1}$
$\delta$NH: 1495 cm$^{-1}$

EXAMPLE 4

N-(2,4,6-Trimethylphenyl)-(6-hydroxy-3,4-dihydro-2,5,7,8-tetramethyl-2H[l]-benzopyran-2,%2-yl)carboxamide The title product is obtained by carrying out the procedure as in Example 2, but replacing the compound from Example 1 by the compound from Example 3:
Yield: 95%
Melting point: 163°–164° C.
Infrared spectra characteristics:
$\nu C=O$: 1670 cm$^{-1}$
$\nu NH$: 3400 cm$^{-1}$
$\nu OH$: 3440 cm$^{-1}$
$\delta NH$: 1500 cm$^{-1}$

EXAMPLE 5

N-Butyl-N-(4,6-dimethylpyridin-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by N-(4,6-dimethylpyridin-2-yl)butylamine:
Yield: 55.6%.

EXAMPLE 6

N-Butyl-N-(4,6-dimethylpyridin-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 5:
Yield: 78%
Melting point: 144°–145° C.
Infrared spectra characteristics:
$\nu C=O$: 1630 cm$^{-1}$
$\nu OH$: 3600–3300 cm$^{-1}$
$\nu C=C, C=N$: 1600, 1560 cm$^{-1}$

EXAMPLE 7

N-(3,4,5-Trimethoxyphenyl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 3,4,5-trimethoxyaniline:
Yield: 91%
Melting point: 65°–85° C.

EXAMPLE 8

N-(3,4,5-Trimethoxyphenyl)-(6-hydroxy-3,4-dihydro-2,5,7,8-tetramethyl-2H[1]-benzopyran-2-yl)carboxamide This title product is obtained by carrying out the procedure as in Example 2, but replacing the compound from Example 1 by the compound from Example 7:
Yield: 88%
Melting point: 154°–156° C.
Infrared spectra characteristics:
$\nu C=O$: 1660 cm$^{-1}$
$\nu NH$: 3400 cm$^{-1}$
$\nu OH=$ 3600–3300 cm$^{-1}$
$\nu C=C$: 1600 cm$^{-1}$
$\delta NH$: 1530 cm$^{-1}$

EXAMPLE 9

N-Hexyl-N-(4,6-dimethylpyridin-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by N-(4,6-dimethylpyridin-2-yl)hexylamine.

EXAMPLE 10

N-Hexyl-N-(4,6-dimethylpyridin-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 9:
Melting point: 114°–115° C.;

EXAMPLE 11

N-Cyclohexylmethyl-N-(4,6-dimethylpyridin-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by N-(4,6-dimethylpyridin-2-yl)cyclohexyl methylamine.

EXAMPLE 12

N-Cyclohexylmethyl-N-(4,6-dimethylpyridin-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 11.

EXAMPLE 13

N-Phenyl-N-(buten-3-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by N-(buten-3-yl)aniline.

EXAMPLE 14

N-Phenyl-N-(buten-3-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 13.

EXAMPLE 15

N-Furfuryl-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by furfurylamine:
Yield: 69.7%
Melting point: 127°–128° C.

EXAMPLE 16

N-Furfuryl-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 15:
Yield: 80.8%
Melting point: 109°–112° C.
Infrared spectra characteristics:
$\nu C=O$: 1655 cm$^{-1}$
$\nu NH$: 3420 cm$^{-1}$
$\nu OH=3550, 3350$ cm$^{-1}$

EXAMPLE 17

N-(4-Hydroxy-2,3-dimethylphenyl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 4-hydroxy-2,3-dimethylaniline:
Yield: 63.7%
Melting point: 230°–232° C.

EXAMPLE 18

N-(4-Hydroxy-2,3-dimethylphenyl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 17:
Yield: 71%
Melting point: 182°–183° C.
Infrared spectra characteristics:
$\nu C=O$ (amide): 1640 cm$^{-1}$
$\nu NH$: 3400 cm$^{-1}$
$\nu OH$: 3500, 3300 cm$^{-1}$
$\delta NH$: 1510 cm$^{-1}$

EXAMPLE 19

N-(5,7-Dimethylnaphthyridin-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 2-amino-5,7-dimethylnaphthyridine:
Yield: 76.8%
Melting point: 205°–207° C.

EXAMPLE 20

N-(5,7-Dimethylnaphthyridin-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 19:
Yield: 86.5%
Melting point: 277°–280° C.
Infrared spectra characteristics:
$\nu C=O$: 1690 cm$^{-1}$
$\nu NH$: 3390 cm$^{-1}$
$\lambda OH$: 3500, 3200 cm$^{-1}$

EXAMPLE 21

N-Cyclopropylmethyl-N-(4,6-dimethylpyridin-2-yl)-(6-acetoxy-3,4-dihydro-2,5,7,8-tetramethyl-2H-[1]-benzopyran-2-yl)carboxamide The title product is obtained by replacing, in stage B of Example 1, N-(4,6-dimethylpyridin-2-yl)isobutylamine by N-(4,6-dimethylpyridin-2-yl)cyclopropylmethylamine and by changing the length of the refluxing stage from 3 hours to 24 hours:
Melting point: 105°–106° C.

EXAMPLE 22

N-Cyclopropylmethyl-N-(4,6-dimethylpyridin-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 21:
Yield: 95.8%
Melting point: 159°–160° C.
Infrared spectra characteristics:
$\nu C=O$: 1630 cm$^{-1}$
$\nu CH_2$ (cyclopropane): 3080 cm$^{-1}$
$\nu CH_2, CH_3$: 2980, 2920, 2950 cm$^{-1}$
$\nu C=C, C=N$: 1605, 1555 cm$^{-1}$

EXAMPLE 23

N-(4-methylquinolin-2-yl)-(6-acetoxy-3,4-dihydro-2,5,7,8-tetramethyl)-2H[1]-benzopyran-2-yl)carboxamide The title product is obtained by replacing, in stage B of Example 1, N-(4,6-dimethylpyridin-2-yl)isobutylamine by 2-amine-4-methylquinoline and by changing the length of the refluxing stage from 3 hours to 24 hours:
Yield: 53.4%
Melting point: 205°–207° C.

EXAMPLE 24

N-(4-Methylquinoline-2-yl)-(6-hydroxy-3,4-dihydro-2,5,7,8-tetramethyl-2H[1]-benzopyran-2-yl)carboxamine The title product is obtained by carrying out the procedure as in Example 2, but replacing the compound from Example 1 by the compound from Example 23:
Yield: 91.7%
Melting point: 275°–277° C.
Infrared spectra characteristics:
$\nu C=O$: 1700 cm$^{-1}$
$\nu NH$: 3380 cm$^{-1}$
$\nu OH$: 3600, 3300 cm$^{-1}$
$\nu C=C, C=N$: 1615, 1600, 1560 cm$^{-1}$
$\delta NH$: 1520 cm$^{-1}$

EXAMPLE 25

N-Phenyl-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by aniline:
Yield: 80.9%
Melting point: 104°–105° C.
Infrared spectra characteristics:
$\lambda C=O$ (ester): 1750 cm$^{-1}$
$\nu C=O$ (amide): 1685 cm$^{-1}$
$\nu NH$: 3400 cm$^{-1}$
$\nu C=C$: 1595 cm$^{-1}$
$\delta NH$: 1520 cm$^{-1}$

EXAMPLE 26

N-Phenyl-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 25:
Yield: 86%
Melting point: 107°–109° C.
Infrared spectra characteristics:
$\nu C{=}O$: 1670 cm$^{-1}$
$\nu NH$: 3400 cm$^{-1}$
$\nu OH$: 3480 cm$^{-1}$
$\nu C{=}C$: 1600 cm$^{-1}$
$\delta NH$: 1520 cm$^{-1}$

EXAMPLE 27

(S)-(−)-N-Phenyl-(6-hydroxy-3,4-dihydro-2,5,7,7-tetramethyl-2H[1]-benzopyran-2-yl)carboxamide Specific rotation $[\alpha]_D^{24} = -262°$.

EXAMPLE 28

(R)-(+)-N-Phenyl-(6-hydroxy-3,4-dihydro-2,5,7,8-tetramethyl-2H[1]-benzopyran-2-yl)carboxamide Specific rotation $[\alpha]_D^{24} = +256°$.

EXAMPLE 29

N-(2-Carboxy-4,5-dimethoxyphenyl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 2-carboxy-4,5-dimethoxyaniline:
Yield: 49.6%
Melting point: 254°–256° C.

EXAMPLE 30

N-(2-Carboxy-4,5-dimethoxyphenyl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 29:
Yield: 65.8%
Melting point: 244° C.
Infrared spectra characteristics:
$\nu C{=}O$ (amide): 1690 cm$^{-1}$
$\nu C{=}O$ (acid): 1660 cm$^{-1}$
$\nu NH$: 3360 cm$^{-1}$
$\nu OH$: 3200 cm$^{-1}$
$\nu C{=}C$: 1615, 1600 cm$^{-1}$
$\delta NH$: 1530 cm$^{-1}$

EXAMPLE 31

N-(3,5-Dichloro-4-hydroxyphenyl)-(6-acetoxy-3,4-dihydro-2,5,7,8-tetramethyl-2H[1]-benzopyran-2-yl)carboxamide The title product is obtained by replacing in stage B of Example 1, N-(4,6-dimethylpyridin-2-yl)isobutylamine by 3,5-dichloro-4-hydroxyaniline:
Yield: 48%
Melting point: 168° C.

EXAMPLE 32

N-(3,5-Dichoro-4-hydroxyphenyl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 31:
Yield: 63%
Melting point: 208° C.
Infrared spectra characteristics:
$\nu C{=}O$: 1680 cm$^{-1}$
$\nu NH$: 3400 cm$^{-1}$
$\nu OH$: 1560, 1470 cm$^{-1}$
$\nu C{=}C$: 1570 cm$^{-1}$
$\delta NH$: 1520 cm$^{-1}$

EXAMPLE 33

N-(2-Carboxy-4,6-dimethylphenyl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 2-carboxy-4,5-dimethylanline:
Yield: 43.7%

EXAMPLE 34

N-(2-Carboxy-4,6-dimethylphenyl)-(6-hydroxy-3,4-dihydro-2,5,7,8-tetramethyl-2H[1]-benzopyran-3-yl)carboxamide The title product is obtained by carrying out the procedure as in Example 2, but replacing the compound from Example 1 by the compound from Example 33:
Yield: 71%
Melting point: 244° C.
Infared spectra characteristics:
$\nu C{=}O$ (amide): 1710 cm$^{-1}$
$\nu C{=}O$ (acid): 1660 cm$^{-1}$
$\nu NH$: 3350 cm$^{-1}$
$\nu OH$: 3500–3200 cm$^{-1}$
$\delta NH$: 1505 cm$^{-1}$

EXAMPLE 35

N-(2,4,5-Trimethylphenyl)-(6-acetoxy-3,4-dihydro-2,4,7,8-tetramethyl-2H[1]-benzopyran-2-yl)carboxamide The title product is obtained by replacing, in stage B of Example 1, N-(4,6-dimethylpyridin-2-yl)isobutylamine by 2,4,5-trimethylaniline:
Yield: 76.5%
Melting point: 168°–162° C.

EXAMPLE 36

N-(2,4,5-Trimethylphenyl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1by the compound from Example 35:
Yield: 64.5%
Melting point: 180°–182° C.
Infrared spectra characteristics:
$\nu C{=}O$: 1670 cm$^{-1}$
$\nu NH$: 3410 cm$^{-1}$
$\nu OH$: 3480 cm$^{-1}$
$\nu C{=}C$: 1580 cm$^{-1}$
$\delta NH$: 1520 cm$^{-1}$

EXAMPLE 37

N-(2-Methylquinolin-4-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 4-amino-2-methylquinoline:
Yield: 52%
Melting point: 210° C.

EXAMPLE 38

N-(2-Methylquinolin-4-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 37:
Yield: 78.7%
Melting point: 273°–275° C.
Infrared spectra characteristics:
$\nu$C=O: 1700 cm$^{-1}$
$\nu$NH: 3380 m$^{-1}$
$\nu$C=C, C=H: 1620, 1600, 1560 cm$^{-1}$
$\delta$NH: 1520 cm$^{-1}$

EXAMPLE 39

1-Oxa-2-oxo-3,8-diaza-8-[(6-acetoxy-3,4-dihydro-2,5,7,8-tetramethyl-2H[1]-benzopyran-2-yl)carbonyl]-spiro[4.5]decane The title product is obtained by replacing, in stage B of Example 1, N-(4,6-dimethylpyridin-2-yl)isobutylamine by 1-oxa-2-oxo-3,8-diaza-spiro[4.5]decane:
Yield: 62.3%
Melting point: 206° C.

EXAMPLE 40

1-Oxa-2-oxo-3,8-diaza-8-[(6-dihydro-3,4-dihydro-2,5,7,8-tetramethyl-2H[1]-benzopyran-2-yl)carbonyl]-spiro[4.5]decane The title product is obtained by carrying out the procedure as in Example 2, but replacing the compound from Example 1 by the compound from Example 39:
Yield: 82.2%
Melting point: 218° C.
Infrared spectra characteristics:
$\nu$C=O: (carbamate): 1740 cm$^{-1}$
$\nu$C=O (amide): 1620 cm$^{-1}$

EXAMPLE 41

N-Isobutyl-N-(4-methylquinolin-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by N-(4-methylquinolin-2-yl)isobutylamine and by changing the length of the refluxing stage from 3 hours to 24 hours.

EXAMPLE 42

N-Isobutyl-N-(4-methylquinolin-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 41.

EXAMPLE 43

N-(1-Methyl-$\beta$-carbolin-3-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 3-amino-1-methyl-$\beta$-carboline.

EXAMPLE 44

N-(1-Methyl-$\beta$-carbolin-3-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 43.

EXAMPLE 45

N-(4-Chloronaphth-1-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 1-amino-4-chloronaphthalene.

EXAMPLE 46

N-(4-Chloronaphth-1-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 45.

EXAMPLE 47

N-(Naphth-2-yl)-(6-acetoxy-3,4-dihydro-2,5,7,8-tetramethyl-2H[1]-benzopyran-2-yl)carboxamide The title product is obtained by replacing, in stage B of Example 11 N-(4,6-dimethylpyridin-2-yl)isobutylamine by 2-aminonaphthalene.

EXAMPLE 48

N-(Naphth-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 47.

EXAMPLE 49

N-(3,4-Dihydro-2H[l]-benzopyran-2-yl)-(6-acetoxy-3,4-dihydro-2,5,7,8-tetramethyl-2H[1]-benzopyran-2-yl)carboxamide The title product is obtained by replacing, in stage B of Example 11 N-(4,6-dimethylpyridin-2-yl) isobutylamine by 2-amino-3,4-dihydro-2H[1]-benzopyran.

EXAMPLE 50

N-(3,4-Dihydro-2H[l]-benzopyran-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 49.

EXAMPLE 51

N-(3,4-Dihydro-2H[1]-pyran-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 2-amino-3,4-dihydro-2H[1]-pyran.

EXAMPLE 52

N-(3,4-Dihydro-2H[1]-pyran-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 51.

EXAMPLE 53

N-(Isoquinolin-5-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 5-aminoisoquinoline.

EXAMPLE 54

N-(Isoquinolin-5-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 53.

EXAMPLE 55

N-(Thiazol-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 2-aminothiazole.

EXAMPLE 56

N-(Thiazol-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 55.

EXAMPLE 57

N-(3-Methylisothiazol-5-yl) - (6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 5-amino-3-methylisothiazole.

EXAMPLE 58

N-(3-Methylisothiazol-5-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 57.

EXAMPLE 59

N-{4-[(2,4-Dioxo-5-thiazolidinyl)methyl]phenyl}-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by N-{4-[(2,4-dioxo-5-thiazolidinyl)methyl]phenyl}amine.

EXAMPLE 60

N-{4-[(2,4-Dioxo-5-thiazolidinyl)methyl]phenyl}-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 59.

Melting point: 108°–112° C.
Infrared spectra characteristics:
$\nu$NH 3400, 3200 cm$^{-1}$
$\nu$C=O 1750, 1690 cm$^{-1}$

EXAMPLE 61

N-(5-Methylisoxazol-3-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 3-amino-5-methylisoxazole.

EXAMPLE 62

N-(5-Methylisoxazol-3-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 61.

EXAMPLE 63

N-[(3-Hydroxyisoxazol-5-yl)methyl]-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by muscimol.

EXAMPLE 64

N-[(3-Hydroxyisoxazol-5-yl)methyl]-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 63.

EXAMPLE 65

N-[(Thien-2-yl)methyl]-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 2-thiophenemethylamine.

EXAMPLE 66

N-[(Thien-2-yl)methyl]-(6-hydroxy-3,4-dihydro-2,5,7,8-tetramethyl-2H[1]-benzopyran-2-yl) carboxamide The title product is obtained by carrying out the procedure as in Example 2, but replacing the compound from Example 1 by the compound from Example 65.

EXAMPLE 67

N-(Benzofuran-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 2-aminobenzofuran.

EXAMPLE 68

N-(Benzofuran-2-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 67.

EXAMPLE 69

N-Butyl-N-phenyl-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by N-butylaniline.

Yield: 50%

Melting point: 135° C.

EXAMPLE 70

N-Butyl-N-phenyl-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 69.

EXAMPLE 71

N-(Naphth-1-yl)-N-phenyl-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by N-phenyl-(naphth-1-yl)amine.

EXAMPLE 72

N-(Naphth-1-yl)-N-phenyl-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 71.

EXAMPLE 73

N-Allyl-N-phenyl-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by N-allylaniline.

EXAMPLE 74

N-Allyl-N-phenyl-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 73.

EXAMPLE 75

N-Cyclopropyl-N-phenyl-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by N-cyclopropylaniline.

EXAMPLE 76

N-Cyclopropyl-N-phenyl-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 75.

EXAMPLES 77 to 102

The following products are similarly obtained by following Examples 1 and 2 and by using the appropriate amines:

EXAMPLE 77

N-Ethyl-N-(4-methylquinolin-2-yl)-(6-acetoxy-3,4-dihydro-2,5,7,8-tetramethyl-2H[1]-benzopyran-2-yl)carboxamide

EXAMPLE 78

N-Ethyl-N-(4-methylquinolin-2-yl)-(6-hydroxy-3,4-dihydro-2,5,7,8-tetramethyl-2H[1]-benzopyran-2-yl)carboxamide

EXAMPLE 79

N-(Buten-3-yl)-N-(4-methylquinolin-2-yl)-(6-acetoxy-3,4-dihydro-2,5,7,8-tetramethyl-2H[1]-benzopyran-2-yl)carboxamide

EXAMPLE 80

N-(Buten-3-yl)-N-(4-methylquinolin-2-yl)-(6-hydroxy-3,4-dihydro-2,5,7,8-tetramethyl-2H[1]-benzopyran-2-yl)carboxamide

EXAMPLE 81

N-Phenyl-N-(4,6-dimethylpyridin-2-yl)-(6-acetoxy-3,4-dihydro-2,5,7,8-tetramethyl-2H[1]-benzopyran-2-yl)carboxamide

EXAMPLE 82

N-Phenyl-N-(4,6-dimethylpyridin-2-yl)-(6-hydroxy-3,4-dihydro-2,5,7,8-tetramethyl-2H[1]-benzopyran-2-yl)carboxamide

EXAMPLE 83

N-(Ethoxyprop-1-yl)-(6-acetoxy-3,4-dihydro-2,5,7,8-tetramethyl-2H[1]-benzopyran-2-yl)carboxamide

EXAMPLE 84

N-(Ethoxyprop-1-yl)-(6-hydroxy-3,4-dihydro-2,5,7,8-tetramethyl-2H[1]-benzopyran-2-yl)carboxamide

EXAMPLE 85

N-(Methoxyethyl)-(6-acetoxy-3,4-dihydro-2,5,7,8-tetramethyl-2H[1]-benzopyran-2-yl)carboxamide

EXAMPLE 86

N-(Methoxyethyl)-(6-hydroxy-3,4-dihydro-2,5,7,8-tetramethyl-2H[1]-benzopyran-2-yl)carboxamide Melting point: 115°–116° C.

EXAMPLE 87

N-Phenyl-N-ethoxycarbonylmethyl-(6-acetoxy-3,4-dihydro-2,5,7,8-tetramethyl-2H[1]-benzopyran-2-yl)carboxamide

EXAMPLE 88

N-Phenyl-N-ethoxycarbonylmethyl-(6-hydroxy-3,4-dihydro-2,5,7,8-tetramethyl-2H[1]-benzopyran-2-yl)carboxamide

EXAMPLE 89

1-[(6-Acetoxy-3,4-dihydro-2,5,7,8-tetramethyl-2H[1]-benzopyran-2-yl)carbonyl]-5,5-dimethylbiguanide

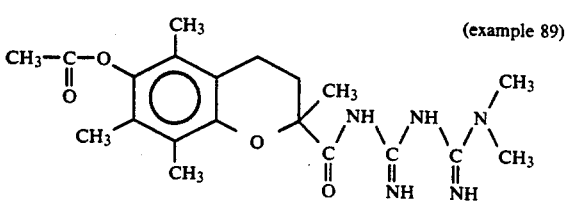
(example 89)

EXAMPLE 90

1-[(6-Hydroxy-3,4-dihydro-2,5,7,8-tetramethyl-2H[1]-benzopyran-2-yl)carbonyl]-5,5-dimethylbiguanide

EXAMPLE 91

N-Guanidino-(6-acetoxy-3,4-dihydro-2,5,7,8-tetramethyl-2H[l]-benzopyran-2-yl)carboxamide

EXAMPLE 92

N-Guanidino-(6-hydroxy-3,4-dihydro-2,5,7,8-tetramethyl-2H[1]-benzopyran-2-yl)carboxamide

EXAMPLE 93

1-[(6-Acetoxy-3,4-dihydro-2,5,7,8-tetramethyl-2H[1]-benzopyran-2-yl)carbonyl]-3,3-dimethylguanidine

EXAMPLE 94

1-[(6-Hydroxy-3,4-dihydro-2,5,7,8-tetramethyl-2H[1]-benzopyran-2-yl)carbonyl]-3,3-dimethylguanidine

EXAMPLE 95

N-[4-Amino-5-(3,4,5-trimethoxybenzyl)-pyrimidin-2-yl]-(6-acetoxy-3,4-dihydro-2,5,7,8-tetramethyl-2H[1]-benzopyran-2-yl)carboxamide

EXAMPLE 96

N-[4-Amino-5-(3,4,5-trimethoxybenzyl)-pyrimidin-2-yl]-(6-hydroxy-3,4-dihydro-2,5,7,8-tetramethyl-2H[1]-benzopyran-2-yl)carboxamide

EXAMPLE 97

N-[4-Amino-5-(4-chlorophenyl)-6-ethylpyrimidin-2-yl]-(6-acetoxy-3,4-dihydro-2,5,7,8-tetramethyl-2H[1]-benzopyran-2-yl)carboxamide

EXAMPLE 98

N-[4-Amino-5-(4-chlorophenyl)-6-ethylpyrimidin-2-yl]-(6-hydroxy-3,4-dihydro-2,5,7,8-tetramethyl-2H[1]-benzopyran-2-yl)carboxamide

EXAMPLE 99

N-{4-[(2-Oxo-1,2,3,5-oxathiadiazol-4-yl)methyl]-phenyl]-(6-acetoxy-3,4-dihydro-2,5,7,8-tetramethyl-2H[1]-benzopyran-2-yl)carboxamide

EXAMPLE 100

N-{4-[(2-Oxo-1,2,3,5-oxathiadiazol-4-yl)methyl]-phenyl}-(6-hydroxy-3,4-dihydro-2,5,7,8-tetramethyl-2H[1]-benzopyran-2-yl)carboxamide

EXAMPLE 101

N-(6-Chlorohexyl)-(6-acetoxy-3,4-dihydro-2,5,7,8-tetramethyl-2H[1]-benzopyran-2-yl)carboxamide

EXAMPLE 102

N-(6-Chlorohexyl)-(6-hydroxy-3,4-dihydro-2,5,7,8-tetramethyl-2H[1]-benzopyran-2-yl)carboxamide

EXAMPLE 103

N-(1,3-Dihydro-2-methylprop-2-yl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl) isobutylamine by 2-amino-2-methyl-1,3-propanediol:
Yield: 60.32%
Melting point: 117°–119° C.
Infrared spectra characteristics:
$\nu$C=O (ester): 1720 cm$^{-1}$
$\nu$C=O (amide): 1660 cm$^{-1}$
$\nu$NH: 3420 cm$^{-1}$
$\delta$NH: 1515 cm$^{-1}$

EXAMPLE 104

N-(2,2,5-Trimethyl-1,3-dioxan-5-yl)-(6-acetoxy-3,4-dihydro-2,5,7,8-tetramethyl-2H[1]-benzopyran-2-yl)carboxamide 3 grams (7.9 mmol) of the compound from Example 103 are dissolved in 45 cm$^3$ of 2,4-dimethoxypropane, 15 cm$^3$ of anhydrous dimethylformamide are added followed by 60 milligrams of para-toluenesulfonic acid. The mixture is refluxed for one hour. Excess 2,2-dimethoxypropane is evaporated under vacuum. The residual mixture is diluted with water. The product is extracted with dichloromethane. The organic phase is washed with a solution of sodium bicarbonate and then with water.

The amide is purified by passage through a silica gel column, eluting with ethyl ether. The title product is obtained:
Yield: 93.5%
Melting point: 97°–99° C.

EXAMPLE 105

N-(2,2,5-Trimethyl-1,3-dioxan-5-yl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 104:
Yield: 87%
Melting point: 153°–154° C.
Infrared spectra characteristics:
$\nu$C=O (amide): 1650 cm$^{-1}$
$\nu$NH: 3410 cm$^{-1}$
$\nu$OH: 3500–3300 cm$^{-1}$
$\delta$NH: 1515 cm$^{-1}$

EXAMPLE 106

N-(4,6-Dimethylpyridin-2-yl)-(6-methoxymethoxy-3,4-dihydro-2,5,7,8-tetramethyl-2H[1]-benzopyran-2-yl)carboxamide

STAGE A (6-Methoxymethoxy-3,4-dihydro-2,5,7,8-tetramethyl-2H[1]-benzopyran-2-yl)carboxylic acid 50 grams (0.2 mol) of (6-hydroxy-3,4-dihydro-2,5,7,8-tetramethyl-2H[1]-benzopyran-2)carboxylic acid are dissolved in 150 cm$^3$ of anhydrous pyridine. 16.34 cm$^3$ (0.2 mol) of bromo methyl methyl ether are added dropwise. The mixture is stirred for 2 hours and the solution is then poured into ice. It is acidified with acetic acid and then extracted with methylene chloride. The organic phase is washed with water and dried over anhydrous sodium sulfate, and the title product is then purified by passage through a silica gel column, eluting with methylene chloride.

STAGE B

N-(4,6-Dimethylpyridin-2-yl)-(6-methoxymethoxy-3,4-dihydro-2,5,7,8-tetramethyl-2H[1]-benzopyran-2-yl)carboxamide 5.4 grams (18.47 mmol) of the compound in stage A of Example 106 are dissolved in 30 cm$^3$ of anhydrous benzene, 2.2 cm$^3$ (27.41 mmol) of thionyl chloride are added, refluxed for 3 hours, and the solvent expelled under vacuum by removing excess thionyl chloride.

The acid chloride thus obtained is dissolved in 30 cm³ of dichloroethane. 2.26 grams (18.5 mmol) of 2-amino-4,6-dimethylpyridine are dissolved, in another vessel, in 20 cm³ of dichloroethane, 7.7 cm³ of triethylamine are added and the above acid chloride solution is poured dropwise into this mixture. After stirring for 8 hours, the solvent is evaporated under vacuum, the residue taken up in 30 cm³ of water, neutralized with a solution of NaHCO₃, extracted with methylene chloride, the organic phase washed with water and then dried over sodium sulfate. After evaporation of the solvent, the product is purified by silica gel chromatography, eluting with methylene chloride.

The title product is obtained
Yield: 60.2%
Melting point: 75°–76° C.
Infrared spectra characteristics:
$\nu C=O$: 1690 cm$^{-1}$
$\nu NH$: 3410 cm$^{-1}$
$\nu CH_2, CH_3$: 2980, 2940, 2860 cm$^{-1}$
$\nu C=C, C=N$ 1610, 1570 cm$^{-1}$
$\delta NH$: 1520 cm$^{-1}$

EXAMPLE 107

N-(4,6-Dimethylpyridin-2-yl)-(6-ethoxycarbonylmethoxy-3,4-dihydro-2,5,7,8-tetramethyl-2H[1]-benzopyran-2-yl)carboxamide The title product is obtained by carrying out the procedure as in Example 106, but replacing, in stage A of Example 106, methyl oxide bromide by ethyl bromoacetate:
Yield: 69.5%
Melting point: 128°–129° C.
Infrared spectra characteristics:
$\nu C=O$ (ester): 1760 cm$^{-1}$
$\nu C=O$ (amide): 1685 cm$^{-1}$
$\nu NH$: 3400 cm$^{-1}$
$\nu CH_2, CH_3$: 2980, 2920, 2860 cm$^{-1}$
$\nu C=C, C=N$ 1620, 1570 cm$^{-1}$
$\delta NH$: 1510 cm$^{-1}$

EXAMPLE 108

N-(4,6-Dimethylpyridin-2-yl)-(6-carboxymethoxy-3,4-dihydro-2,5,7,8-tetramethyl-2H[1]-benzopyran-2-yl)carboxamide 1.77 grams (4 mmol) of the compound from Example 107 are dissolved in 40 cm³ of ethanol. 4 cm³ of 2N sodium hydroxide are added dropwise. The reaction mixture is stirred for 2 hours and then diluted with 60 cm³ of water, and acidified with acetic acid. It is filtered, washed with water and then dried. 1.55 grams of the title product are obtained:
Melting point: 230°–231° C.
Infrared spectra characteristics:
$\nu C=O$ (acid): 1730 cm$^{-1}$
$\nu C=O$ (amide): 1700 cm$^{-1}$
$\nu NH$: 3400 cm$^{-1}$
$\nu CH_2, CH_3$: 2980, 2920, 2860 cm$^{-1}$
$\nu C=C, C=N$: 1620, 1570 cm$^{-1}$
$\delta NH$: 19520 cm$^{-1}$

EXAMPLE 109

N-(4,6-Dimethylpyridin-2-yl)-(6-ethoxyethoxy-3,4-dihydro-2,5,8-tetramethyl-2H[1]-benzopyran-2-yl)carboxamide The title product is obtained by carrying out the procedure as in Example 106, but replacing, in stage A of Example 106, methyl oxide bromide by ethyl oxide bromide;
Melting point: 96°–98° C.

EXAMPLE 110

N-(4,6-Dimethylpyridin-2-yl)-(6-ethoxycarbonyloxy-3,4-dihydro-2,5,7,8-tetramethyl-2H[1]-benzopyran-2yl)-carboxamide The title product is obtained by carrying out the procedure as in Example 106, but replacing, in stage A of Example 106, methyl oxide bromide by ethyl bromate:
Yield: 63%
Melting point: <50° C.
Infrared spectra characteristics:
$\nu C=O$ (ester): 1760 cm$^{-1}$
$\nu C=O$ (amide): 1700 cm$^{-1}$
$\nu NH$: 3410 cm$^{-1}$
$\nu CH$ (CH₂, CH₃): 2980, 2940, 2880 cm$^{-1}$
$\nu C=C, C=N$: 1610, 1570 cm$^{-1}$
$\delta NH$: 1520 cm$^{-1}$

EXAMPLE 111

N-(4-Methylquinolin-2-yl)-(6-methoxymethoxy-3,4-dihydro-2,5,7,8-tetramethyl-2H[1]-benzopyran-2-yl)carboxamide The title product is obtained by replacing, in stage B of Example 106, 2-amino-4,6-dimethylpyridine by 2-amino-4-methylquinoline.

EXAMPLES 112 TO 115

Similarly, by replacing, in stage B of Example 106, 2-amino-4,6-dimethylpyridine by 2-amino-4-methylquinoline and by carrying out the procedures as in examples from 108 to 110, the following products are obtained.

EXAMPLE 113

N-(4-Methylquinolin-2-yl)-(6-carboxymethoxy-3,4-dihydro-2,5,7,8-tetramethyl-2H[1]-benzopyran-2-yl)carboxamide

EXAMPLE 114

N-(4-Methylquinolin-2-yl)-(6-ethoxyethoxy-3,4-dihydro-2,5,7,8-tetramethyl-2H[1]-benzopyran-2-yl)carboxamide

EXAMPLE 115

N-(4-Methylquinolin-2-yl)-(6-ethoxycarbonyloxy-3,4-dihydro-2,5,7,8-tetramethyl-2H[1]-benzopyran-2-yl)carboxamide

EXAMPLE 116

N-Phenyl-(6-methoxymethoxy-3,4-dihydro-2,5,7,8-tetramethyl-2H[1]-benzopyran-2-yl)carboxamide The title product is obtained by replacing, in stage B of Example 106, 2-amino-4,6-dimethylpyridine by aniline.

EXAMPLES 117 to 120

The products from the following examples are similarly obtained by replacing, in stage B of Example 106, 2-amino- 4,6-dimethylpyridine by aniline and by following the procedures described in Examples 107 to 110:

EXAMPLE 117

N-Phenyl-(6-ethoxycarbonylmethoxy-3,4-dihydro-2,5,7,8-tetramethyl-2H[1]-benzopyran-2-yl)carboxamide

EXAMPLE 118

N-Phenyl-(6-carboxymethoxy-3,4-dihydro-2,5,7,8-tetramethyl-2H[1]-benzopyran-2-yl)carboxamide

EXAMPLE 119

N-Phenyl-(6-ethoxyethoxy-3,4-dihydro-2,5,7,8-tetramethyl-2H[1]-benzopyran-2-yl)carboxamide

EXAMPLE 120

N-Phenyl-(6-ethoxycarbonyloxy-3,4-dihydro-2,5,7,8-tetramethyl-2H[1]-benzopyran-2-yl)carboxamide

EXAMPLE 121

N-(4-Methylquinolin-2-yl)-[(6-hydroxy-3,4-dihydro-2,5,7,8-tetramethyl-2H[1]-benzopyran-2-yl)methyl]amine 2.2 grams (5.6 mmol) of the compound from Example 24 are dissolved in 120 cm3 of anhydrous tetrahydrofuran, 0.94 gram of lithium and aluminum hydride is added and the mixture is then refluxed for 3 hours.

After cooling, the mixture is poured into ice, filtered and the product extracted with hot chloroform. The organic phase is dried over sodium sulfate. After removing the solvent, the oily residue is triturated to give the title product:
  Infrared spectra characteristics
  $\nu$NH: 3380 cm$^{-1}$
  $\nu$CH: 2970, 2920 cm$^{-1}$
  $\nu$OH: 3600, 3300 cm$^{-1}$
  $\nu$C=C,C=N 1615, 1600, 1560 cm$^{-1}$
  Melting point: 196°–198° C.

EXAMPLE 122

N-(4-Methylquinolin-2-yl)-[(6-acetoxy-3,4-dihydro-2,5,7,8-tetramethyl-2H[1]-benzopyran-2-yl)methyl]amine The title product is obtained by carrying out the procedure as in stage A of Example 1, but replacing (6-hydroxy-3,4-dihydro-2,5,7,8-tetramethyl-2H[1]-benzopyran-2-yl)carboxylic acid by the compound from Example 121.

EXAMPLE 123

N-Isobutyl-N-(4-methylquinolin-2-yl)-[(6-hydroxy-3,4-dihydro-2,5,7,8-tetramethyl-2H[1]-benzopyran-2-yl)methyl]amine The title product is obtained by carrying out the procedure as in Example 121, but replacing the compound from Example 24 by the compound from Example 42.

EXAMPLE 124

N-Isobutyl-N-(4-methylquinolin-2-yl)-[(6-acetoxy-3,4-dihydro-2,5,7,8-tetramethyl-2H[1-benzopyran-2-yl)methyl]amine The title product is obtained by carrying out the procedure as in stage A of Example 1, but replacing (6-hydroxy-3,4-dihydro-2,5,7,8-tetramethyl-2H[1]-benzopyran-2-yl)carboxylic acid by the compound from Example 123.

EXAMPLE 125

N-(4,6-Dimethylpyridin-2-yl)-[(6-ethoxyethoxy-3,4-dihydro-2,5,7,8-tetramethyl-2H[1]-benzopyran-2-yl)methyl]amine The title product is obtained by carrying out the procedure as in Example 121, but replacing the compound from Example 24 by the compound from Example 109.

EXAMPLE 126 TO 147

The following title products are similarly obtained by carrying out the procedure as in Example 121, but replacing the compound from Example 24 by the compound from Example 1, 2, 3, 4, 5, 6, 21, 22, 55, 56, 69, 70, 71, 72, 73, 74, 104, 105, 106, 107, 108 and 110 respectively:

EXAMPLE 126

N-Isobutyl-N-(4,6-dimethylpyridin-2-yl)-[(6-acetoxy-3,4-dihydro-2,5,7,8-tetramethyl-2H[1]-benzopyran-2-yl)methyl]amine

EXAMPLE 127

N-Isobutyl-N-(4,6-dimethylpyridin-2-yl)-[(6-hydroxy-3,4-dihydro-2,5,7,8-tetramethyl-2H[1]-benzopyran-2-yl)methyl]amine

EXAMPLE 128

N-(2,4,6-Trimethylphenyl)-[(6-acetoxy-3,4-dihydro-2,5,7,8-tetramethyl-2H[1]-benzopyran-2-yl)methyl]amine

EXAMPLE 129

N-(2,4,6-Trimethylphenyl)-[(6-hydroxy-3,4-dihydro-2,5,7,8-tetramethyl-2H[1]-benzo-pyran-2-yl)methyl]amine

EXAMPLE 130

N-Butyl-N-(4,6-dimethylpyridin-2-yl)-[(6-acetoxy-3,4,-dihydro-2,5,7,8-tetramethyl-2H[1]-benzopyran-2-yl)methyl]amine

EXAMPLE 131

N-Butyl-N-(4,6-dimethylpyridin-2-yl)-[(6-hydroxy-3,4-dihydro-2,5,7,8-tetramethyl-2H[1]-benzopyran-2-yl)methyl]amine

EXAMPLE 132

N-Cyclopropylmethyl-N-(4,6-dimethylpyridin-2-yl)-[(6-acetoxy-3,4-dihydro-2,5,7,8-tetramethyl-2H[1]-benzopyran-2-yl)methyl]amine

EXAMPLE 133

N-Cyclopropylmethyl-N-(4,6-dimethylpyridin-2-yl)-[(6-hydroxy-3,4-dihydro-2,5,7,8-tetramethyl-2H[1]-benzopyran-2-yl)methyl]amine

EXAMPLE 134

N-(Thiazol-2-yl)-[(6-acetoxy-3,4-dihydro-2,5,7,8-tetramethyl-2H[1]-benzopyran-2-yl)methyl]amine

EXAMPLE 135

N-(Thiazol-2-yl)-[(6-hydroxy-3,4-dihydro-2,5,7,8-tetramethyl-2H[1]-benzopyran-2-yl)methyl]amine

EXAMPLE 136

N-Butyl-N-phenyl-[(6-acetoxy-3,4-dihydro-2,5,7,8-tetramethyl-2H[1]-benzopyran-2-yl)methyl]amine

EXAMPLE 137

N-Butyl-N-phenyl-[(6-hydroxy-3,4-dihydro-2,5,7,8-tetramethyl-2H[1]-benzopyran-2-yl)methyl]amine

EXAMPLE 138

N-(Naphth-1-yl)-N-phenyl-[(6-acetoxy-3,4-dihydro-2,5,7,8-tetramethyl-2H[1]-benzopyran-2-yl)methyl]amine

EXAMPLE 139

N-(Naphth-1-yl)-N-phenyl-[(6-hydroxy-3,4-dihydro-2,5,7,8-tetramethyl-2H[1]-benzopyran-2-yl)methyl]amine

EXAMPLE 140

N-Allyl-N-phenyl-[(6-acetoxy-3,4-dihydro-2,5,7,8-tetramethyl-2H[1]-benzopyran-2-yl)methyl]amine

EXAMPLE 141

N-Allyl-N-phenyl-[(6-hydroxy-3,4-dihydro-2,5,7,8-tetramethyl-2H[1]-benzopyran-2-yl)methyl]amine

EXAMPLE 142

N-(2,2,5-Trimethyl-1,3-dioxan-5-yl)-[(6-acetoxy-3,4-dihydro-2,5,7,8-tetramethyl-2H[1]-benzopyran-2-yl)methyl]amine

EXAMPLE 143

N-(2,2,5-Trimethyl-1,3-dioxan-5-yl)-[(6-hydroxy-3,4-dihydro-2,5,7,8-tetramethyl-2H[1]-benzopyran-2-yl)methyl]amine

EXAMPLE 144

N-(4,6-Dimethylpyridin-2-yl)-(6-methoxymethoxy-3,4-dihydro-2,5,7,8-tetramethyl-2H[1]-benzopyran-2-yl)methyl]amine

EXAMPLE 145

N-(4,6-Dimethylpyridin-2-yl)-[(6-ethoxycarbonylmethoxy-3,4-dihydro-2,5,7,8-tetramethyl-2H[1]-benzopyran-2-yl)methyl]amine

EXAMPLE 146

N-(4,6-Dimethylpyridin-2-yl)-[(6-carboxymethoxy-3,4-dihydro-2,5,7,8-tetramethyl-2H[1]-benzopyran-2-yl)methyl]amine

EXAMPLE 147

N-(4,6-Dimethylpyridin-2-yl)-[(6-ethoxycarbonyloxy)-3,4-dihydro-2,5,7,8-tetramethyl-2H[1]-benzopyran-2-yl)methyl]amine

EXAMPLE 148

N-(4-Methylquinolin-2-yl)-2-(6-acetoxy-3,4-dihydro-2,5,7,8-tetramethyl-2H[1]-benzopyran-2-yl)acetamide The title product is obtained by carrying out the procedure as in Example 1, but replacing, in stage A of Example 1, (6-hydroxy-3,4-dihydro-2,5,7,8-tetramethyl-2H[1]-benzopyran-2-yl)carboxylic acid by (6-hydroxy-3,4-dihydro-2,5,7,8-tetramethyl-2H[1]-benzopyran-2-yl)acetic acid and by replacing, in stage B of Example 1, N-(4,6-dimethylpyridin-2-yl)isobutylamine by 2-amino-4-methylquinoline, as well as by replacing, in the same stage B of Example 1, the refluxing stage, after mixing the solution of acid chloride and amine, by stirring for 24 hours at a temperature of 20° C.:

Infrared spectra characteristics:

$\nu C=O$ (ester): 1760 cm$^{-1}$ $\nu C=O$ (amide): 1690 cm$^{-1}$ $\nu NH$: 3360 cm$^{-1}$ $\nu CH_2, CH_3$: 2990, 2940, 2880 cm$^{-1}$ $\nu C=C, C=N$ 1610, 1600, 1560 cm$^{-1}$ $\delta NH$: 1520 cm$^{-1}$

EXAMPLES 149 TO 155

The products from the following examples are obtained successively by following the procedures described in Example 148, but replacing, in stage B of Example 1, N-(4,6-dimethylpyridin-2-yl)isobutylamine by the appropriate amine:

EXAMPLE 149

N-Isobutyl-N-(4,6-dimethylpyridin-2-yl)-2-(6-acetoxy-3,4-dihydro-2,5,7,8-tetramethyl-2H[1]-benzopyran-2-yl)acetamide

EXAMPLE 150

N-(2,4,6-Trimethylphenyl)-2-(6-acetoxy-3,4-dihydro-2,5,7,8-tetramethyl-2H[1]-benzopyran-2-yl)acetamide

EXAMPLE 151

N-(3,4,5-Trimethoxyphenyl)-(6-acetoxy-3,4-dihydro-2,5,7,8-tetramethyl-2H[1]-benzopyran-2-yl)acetamide

EXAMPLE 152

N-Hexyl-N-(4,6-dimethylpyridin-2-yl)-2-(6-acetoxy-3,4-dihydro-2,5,7,8-tetramethyl-2H[1]-benzopyran-2-yl)acetamide

EXAMPLE 153

N-Phenyl-N-(buten-3-yl)-2-(6-acetoxy-3,4-dihydro-2,5,7,8-tetramethyl-2H[1]-benzopyran-2-yl)acetamide

EXAMPLE 154

N-Isobutyl-N-(4-methylquinolin-2-yl)-2-(6-acetoxy-3,4-dihydro-2,5,7,8-tetramethyl-2H[1]-benzopyran-2-yl)acetamide

EXAMPLE 155

N-Allyl-N-phenyl-2-(6-acetoxy-3,4-dihydro-2,5,7,8-tetramethyl-2H[1]-benzopyran-2-yl)acetamide

EXAMPLE 156 to 163

The products from the following examples are obtained successively by carrying out the procedure as in Example 2, but replacing the compound from Example 1 by the compound 148, 149, 150, 151, 152, 153, 154 and 155:

EXAMPLE 156

N-(4-Methylquinolin-2-yl)-2-(6-hydroxy-3,4-dihydro-2,5,7,8-tetramethyl-2H[1]-benzopyran-2-yl)acetamide

EXAMPLE 157

N-Isobutyl-N-(4,6-dimethylpyridin-2-yl)-2-(6-hydroxy-3,4-dihydro-2,5,7,8-tetramethyl-2H[1]-benzopyran-2-yl)acetamide

EXAMPLE 158

N-(2,4,6-Trimethylphenyl)-2-(6-hydroxy-3,4-dihydro-2,5,7,8-tetramethyl-2H[1]-benzopyran-2-yl)acetamide

EXAMPLE 159

N-(3,4,5-Trimethoxyphenyl)-2-(6-hydroxy-3,4-dihydro-2,5,7,8-tetramethyl-2H[1]-benzopyran-2-yl)acetamide

EXAMPLE 160

N-Hexyl-N-(4,6-dimethylpyridin-2-yl)-2-(6-hydroxy-3,4-dihydro-2,5,7,8-tetramethyl-2H[1]-benzopyran-2-yl)acetamide

EXAMPLE 161

N-Phenyl-N-(buten-3-yl)-2-(6-hydroxy-3,4-dihydro-2,5,7,8-tetramethyl-2H[1]-benzopyran-2-yl)acetamide

EXAMPLE 162

N-Isobutyl-N-(4-methylquinolin-2-yl)-2-(6-hydroxy-3,4-dihydro-2,5,7,8-tetramethyl-2H[1]-benzopyran-2-yl)acetamide

EXAMPLE 163

N-Allyl-N-phenyl-2-(6-hydroxy-3,4-dihydro-2,5,7,8-tetramethyl-2H[1]-benzopyran-2-yl)acetamide

EXAMPLE 164

N-(4,6-Dimethylpyridin-2-yl)-2-(6-methoxymethoxy-3,4-dihydro-2,5,7,8-tetramethyl-2H[1]-benzopyran-2-yl)acetamide The title product is obtained by following the procedures described in Example 106, but replacing, in stage A of Example 106, (6-hydroxy-3,4-dihydro-2,5,7,8-tetramethyl-2H[1]-benzopyran-2-yl)carboxylic acid by (6-hydroxy-3,4-dihydro-2,5,7,8-tetramethyl-2H[l])-benzopyran-2-yl)acetic acid.

EXAMPLES 165 to 168

Similarly, the products from the following examples are obtained successively by replacing, in stage A of Example 106, (6-hydroxy-3,4-dihydro-2,5,7,8-tetramethyl-2H[1]-benzopyran-2-yl)carboxylic acid by (6-hydroxy-3,4-dihydro-2,5,7,8-tetramethyl-2H[1]-benzopyran-2-yl)acetic acid, and by following the instructions for Examples 107 to 110:

EXAMPLE 165

N-(4,6-Dimethylpyridin-2-yl)-2-(6-ethoxycarbonylmethoxy-3,4-dihydro-2,5,7,8-tetramethyl-2H[1]-benzopyran-2-yl)acetamide

EXAMPLE 166

N-(4,6-Dimethylpyridin-2-yl)-2-(6-carboxymethoxy-3,4-dihydro-2,5,7,8-tetramethyl-2H[19-benzopyran-2-yl)acetamide

EXAMPLE 167

N-(4,6-Dimethylpyridin-2-yl)-2-(6-ethoxyethoxy-3,4-dihydro-2,5,7,8-tetramethyl-2H[1]-benzopyran-2-yl)acetamide

EXAMPLE 168

N-(4,6-Dimethylpyridin-2-yl)-2-(6-ethoxycarbonyloxy-3,4-dihydro-2,5,7,8-tetramethyl-2H[1]-benzopyran-2-yl)acetamide

EXAMPLES 169 to 181

The compounds from the following examples are obtained respectively by carrying out the procedure as in Example 121, but replacing successively the compound from Example 24 by the compounds from Examples 156 to 168:

EXAMPLE 169

N-(4-Methylquinolin-2-yl)-2-(6-hydroxy-3,4-dihydro-2,5,7,8-tetramethyl-2H[1]-benzopyran-2-yl)ethylamine

EXAMPLE 170

N-Isobutyl-N-(4,6-dimethylpyridin-2-yl)-2-(6-hydroxy-3,4-dihydro-2,5,7,8-tetramethyl-2H[1]-benzopyran-2-yl)ethylamine

EXAMPLE 171

N-(2,4,6-Trimethylphenyl)-2-(6-hydroxy-3,4-dihydro-2,5,7,8-tetramethyl-2H[1]-benzopyran-2-yl)ethylamine

EXAMPLE 172

N-(3,4,5-Trimethoxyphenyl)-2-(6-hydroxy-3,4-dihydro-2,5,7,8-tetramethyl-2H[1]-benzopyran-2-yl)ethylamine

EXAMPLE 173

N-Hexyl-N-(4,6-dimethylpyridin-2-yl)-2-(6-hydroxy-3,4-dihydro-2,5,7,8-tetramethyl-2H[1]-benzopyran-2-yl)ethylamine

EXAMPLE 174

N-Phenyl-N-(buten-3-yl)-2-(6-hydroxy-3,4-dihydro-2,5,7,8-tetramethyl-2H[1]-benzopyran-2-yl)ethylamine

EXAMPLE 175

N-Isobutyl-N-(4-methylquinolin-2-yl)-2-(6-hydroxy-3,4-dihydro-2,5,7,8-tetramethyl-2H[1]-benzopyran-2-yl)ethylamine

EXAMPLE 176

N-Allyl-N-phenyl-2-(6-hydroxy-3,4-dihydro-2,5,7,8-tetramethyl-2H[1]-benzopyran-2-yl)ethylamine

EXAMPLE 177

N-(4,6-Dimethylpyridin-2-yl)-2-(6-methoxymethoxy-3,4-dihydro-2,5,7,8-tetramethyl-2H[1]-benzopyran-2-yl)ethylamine

EXAMPLE 178

N-(4,6-Dimethylpyridin-2-yl)-2-(6-ethoxycarbonylmethoxy-3,4-dihydro-2,5,7,8-tetramethyl-2H[1]-benzopyran-2-yl)ethylamine

EXAMPLE 179

N-(4,6-Dimethylpyridin-2-yl)-2-(6-carboxymethoxy-3,4-dihydro-2,5,7,8-tetramethyl-2H[1]-benzopyran-2-yl)ethylamine

EXAMPLE 180

N-(4,6-Dimethylpyridin-2-yl)-2-(6-ethoxyethoxy-3,4-dihydro-2,5,7,8-tetramethyl-2H[1]-benzopyran-2-yl)ethylamine

EXAMPLE 181

N-(4,6-Dimethylpyridin-2-yl)-2-(6-ethoxycarbonyloxy-3,4-dihydro-2,5,7,8-tetramethyl-2H[1]-benzopyran-2-yl)ethylamine

EXAMPLE 182

N-(4-methylquinolin-2-yl)-(6-acetoxy-3,4-dihydro-5,7,8-trimethyl-2H[1]-benzopyran-2-yl)carboxamide The title product is obtained by carrying out the procedure as in Example 1, but replacing, in stage A of Example 1 (6-hydroxy-3,4-dihydro-2,5,7,8-tetramethyl-2H[1]-benzopyran-2-yl)carboxylic acid by (6-hydroxy-3,4-dihydro-5,7,8-trimethyl-2H[1]-benzopyran-2-yl)carboxylic acid and by replacing, in stage B of Example 1, N-(4,6-dimethylpyridin-2-yl)isobutylamine by 2-amino-4-methylquinoline, as well as by replacing, in the same stage B of Example 1, the refluxing stage, after mixing the solution of acid chloride and amine, by stirring for 24 hours at a temperature of 20° C.

EXAMPLE 183 to 185

The products from the following examples are obtained successively by following the procedures described in Example 182, but replacing, in stage B of Example 1, N-(4,6-dimethylpyridin-2-yl)isobutylamine by the appropriate amine:

EXAMPLE 183

N-Isobutyl-N-(4-methylquinolin-2-yl)-(6-acetoxy-3,4-dihydro-5,7,8-trimethyl-2H[1]-benzopyran-2-yl)carboxamide

EXAMPLE 184

N-Phenyl-N-(4,6-dimethylpyridin-2-yl)-(6-acetoxy-3,4-dihydro-5,7,8-trimethyl-2H[1]-benzopyran-2-yl)carboxamide

EXAMPLE 185

N-Phenyl-N-(buten-3-yl)-(6-acetoxy-3,4-dihydro-5,7,8-trimethyl-2H[1]-benzopyran-2-yl)carboxamide

EXAMPLES 186 to 189

The products from the following examples are obtained successively by carrying out the procedure as in Example 2, but replacing the compound from Example 1 by the compound from Example 182, 183, 184 and 185:

EXAMPLE 186

N-(4-Methylquinolin-2-yl)-(6-hydroxy-3,4-dihydro-5,7,8-trimethyl-2H[1]-benzopyran-2-yl)carboxamide

EXAMPLE 187

N-Isobutyl-N-(4-methylquinolin-2-yl)-(6-hydroxy-3,4-dihydro-5,7,8-trimethyl-2H[1]-benzopyran-2-yl)carboxamide

EXAMPLE 188

N-Phenyl-N-(4,6-dimethylpyridin-2-yl)-(6-hydroxy-5,7,8-trimethyl-2H[1]-benzopyran-2-yl)carboxamide

EXAMPLE 189

N-Phenyl-N-(buten-3-yl)-(6-hydroxy-3,4-dihydro-5,7,8-trimethyl-2H[1]-benzopyran-2-yl)carboxamide

EXAMPLE 190

N-Phenyl-[(6-hydroxy-3,4-dihydro-2,5,7,8-tetramethyl-2H[1]-benzopyran-2-yl)methyl]amine The title product is obtained by carrying out the procedure as in Example 121, but replacing the compound from Example 24 by the compound from Example 25:

Melting point (maleate): 135° C.

EXAMPLE 191

N-(2,6-Dimethylphenyl)-(6-acetoxy-3,4-dihydro-2,5,7,8-tetramethyl-2H[1]-benzopyran-2-yl)carboxamide The title product is obtained by replacing, in stage B of Example 1, N-(4,6-dimethylpyridin-2-yl)isobutylamine by 2,5-dimethylaniline.

EXAMPLE 192

N-(2,6-Dimethylphenyl)-(6-hydroxy-3,4-dihydro-2,5,7,8-tetramethyl-2H[1]-benzopyran-2-yl)carboxamide The title product is obtained by carrying out the procedure as in Example 2, but replacing the compound from Example 1 by the compound from Example 191:
Yield: 61%
Melting point: 170° C.
Infrared spectra characteristics:
$\nu$OH,NH: 3400, 336.0 cm$^{-1}$
$\nu$CH$_3$: 2970, 2910, 2850 cm$^{-1}$
$\nu$C=C: 1670 cm$^{-1}$
$\nu$C=C: 1605, 1585, 1590 cm$^{-1}$

EXAMPLE 193

N-Phenyl-(6-acetoxy-3,4-dihydro-2-methyl-7-tert-butyl-2H[1]-benzopyran-2-yl)carboxamide The title product is obtained by carrying out the procedure as in Example 1, but replacing, in stage A of Example 1 (6-hydroxy-3,4-dihydro-2,5,7,8-tetramethyl-2H[1]-benzopyran-2-yl)carboxylic acid by (6-hydroxy-3,4-dihydro-2-methyl-7-tert-butyl-2H[1]-benzopyran-2-yl)carboxylic acid and by replacing, in stage B of Example 1, N-(4,6-dimethylpyridin-2-yl)isobutylamine by aniline.

EXAMPLE 194

N-Phenyl-(6-hydroxy-3,4-dihydro-2-methyl-7-tert-butyl-2H[1]-benzopyran-2-yl)carboxamide The title product is obtained by carrying out the procedure as in Example 2, but replacing the compound from Example 1 by the compound from Example 193:
Melting point: 129°-131° C.
Infrared spectra characteristics:
$\nu$NH,OH: 3380, 3330 cm$^{-1}$
$\nu$CH$_3$: 2940, 2860 cm$^{-1}$
$\nu$C=O: 1655 cm$^{-1}$
$\nu$C=C: 1615, 1590 cm$^{-1}$

PHARMACOLOGICAL STUDY OF THE COMPOUNDS OF THE INVENTION (The compounds are compared with the most related prior art compound which is Example 102 of Application WO 88/ 08424)

EXAMPLE 195

Study of the Antiperoxidant Activity

The action of the compounds of the invention, which are capable of trapping -OH radicals was studied, on the one hand, on the spontaneous peroxidation of lipids and, on the other hand, on the peroxidation induced by the system Fe2+-ascorbate (10 µM-250 µM), and this on rat brain homogenates.

During the measurement of spontaneous lipid peroxidation, the rat brain homogenates are placed in the presence or in the absence of the test compounds for 60 minutes at 37° C. The reaction is stopped at 0° C. and the assay of malondialdehyde is carried out using thiobarbituric acid, by the method of YAGI, K (1976) Biochem. Med, 15, 212-216. The lipid peroxidation is determined by the substances reacting with thiobarbituric acid, expressed as nanomoles of malonodialdehyde.

During the measurement of induced lipid peroxidation, the methodology is identical to the above except for the addition to the homogenate of the radical-inducing system: Fe2+- ascorbate. The reference substances are probucol and vitamin E.

The concentrations of the test compounds inhibiting peroxidation of the substrate by 50% are calculated.

It is evident that some compounds of the invention possess a particularly intense antiperoxidant activity since it is greater than that for the most related prior art compound by a factor of 100. This very useful result is produced whether the peroxidation is spontaneous or induced by a chemical system.

EXAMPLE 196

Study of the Protective Power Against the Oxidation of LDLs

The capacity of the compounds of the invention to reduce the proportions of oxidized LDLs was measured in the following manner. A combination of native LDLS, a free radical-generating system Cu2+ and the test compounds were incubated for 24 hours.

The results are obtained after analyzing the mixture using a high-performance chromatographic technique: FPLC (fast protein liquid chromatography). The protective power of the test compound is determined after comparison of the chromatogram obtained with that of the reference positive control: probucol.

It is clearly evident that the compounds of the invention have a protecting power which is very high and substantially greater than that for the most related prior art compound.

EXAMPLE 197

Study of the Inhibitory Activity of the Compounds of the Biosynthesis of Eicosanoids Investigation of the inhibitory activity of the compounds on the biosynthesis of eicosanoids was performed on human platelets previously activated with thrombin and added to the test products.

The production of thromboxane B2, which is a major eicosanoid produced by platelets, is determined by radioimmunological assay (RIA).

The compounds of the invention substantially inhibit the production of thromboxane B2 whereas the most related prior art compound has no effect on this production.

EXAMPLE 198

Pharmaceutical Composition : Tablets

Tablets containing a dose of 50 mg of N-isobutyl-N-(4,6-dimethylpyridin-2-yl)-(6-hydroxy-3,4-dihydro-2,5,7,8-tetramethyl-2H[1]-benzopyran-2-yl)carboxamide

| Preparation formula for 1,000 tablets: | |
|---|---|
| N-isobutyl-N-(4,6-dimethylpyridin-2-yl)-(6-hydroxy-3,4-dihydro-2,5,7,8-tetramethyl-2H[1]-benzopyran-2-yl)carboxamide | 50 g |
| wheat starch | 15 g |
| corn starch | 15 g |
| lactose | 65 g |
| magnesium stearate | 2 g |
| silica | 1 g |
| hydroxypropyl cellulose | 2 g |

We claim:
1. A compound selected from the group consisting of those of the formula (I):

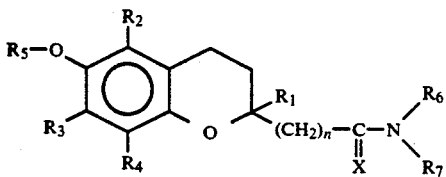

(I)

in which:

n represents 0 or 1,

X represents oxygen or 2 hydrogen, atoms $R_1$, $R_2$, $R_3$, and $R_4$, which are identical or different, each represent independently of one another hydrogen or lower alkyl $R_a$—, where $R_a$ represents linear or branched alkyl having 1 to 8 inclusive carbon atoms, $R_5$ represents:
hydrogen,
lower alkyl group $R_a$—,
lower acyl $R_a$—CO—,
alkoxyalkyl $R_a$—O—$R_b$—,
alkoxycarbonyl $R_a$—O—CO—,
alkoxycarbonylalkyl $R_a$—O—CO—$R_b$—,
carboxyalkyl HOOC—$R_a$—, where $R_a$ and $R_b$, which are identical or different, each represent independently of one another, linear or branched alkyl having 1 to 8 inclusive carbon atoms, $R_6$ and $R_7$ form together with the nitrogen atom carrying them an E group or a substituted E group, wherein E is 1-oxa-2-oxo-3,8-diaza-spiro[4,5]-decan-8-yl, or which are identical or different, each representing independently of one another:
hydrogen,
lower alkyl $R_a$- or substituted lower alkyl $R_a$—,
lower alkenyl or substituted lower alkenyl where alkenyl represents an unsaturated, linear or branched hydrocarbon having 2 to 8 inclusive carbon atoms, a group A-(CH$_2$)$_m$- or a substituted group A-(CH$_2$)$_m$-, where m is 0, 1, or 2 and A represents cycloalkyl having p carbon atoms with p being 3, 4, 5, 6, or 7, it being understood that if p is 3 or 4 then m may be 0, 1, or 2 and if p is 5, 6, or 7 then m can only be 1 or 2, a group phenyl-(CH$_2$)$_q$— or a substituted group phenyl-(CH$_2$)$_q$—, with q as defined above, a group heteroaryl-(CH$_2$)$_q$— or a substituted group heteroaryl-(CH$_2$)$_q$—, with q as defined above and where the heteroaryl is selected from: quinoline, isoquinoline and pyridine, it being understood that when one of the substituents $R_6$ or $R_7$ represents hydrogen, lower alkyl having not more than 3 inclusive carbon atoms, an unsubstituted group phenyl-(CH$_2$)$_q'$—, a group phenyl-(CH$_2$)$_q'$— which is substituted by 1 or 2 radicals, an unsubstituted group pyridinyl-(CH$_2$)$_q$—, or a group pyridinyl-(CH$_2$)$_q$— which is substituted by 1 or 2 radicals, with q as defined above and q' being 1, 2, or 3, then at least one of the following 2 conditions is true:
either the other substituent, $R_6$ or $R_7$ as appropriate, does not represent: hydrogen, lower alkyl having not more than 3 inclusive carbon atoms, an unsubstituted group phenyl-(CH$_2$)$_q'$—, a group phenyl-(CH$_2$)$_q'$— which is substituted by 1 or 2 radicals, an unsubstituted group pyridinyl-(CH$_2$)$_q$—, a group pyridinyl-(CH$_2$)$_q$— which is substituted by 1 to 2 radicals, with q and q' as defined above, or the substituent R5 does not represent hydrogen, lower alkyl having not more than 4 inclusive carbon atoms, or lower acryl R'$_5$—CO—, with R'$_5$ representing lower alkyl having not more than 4 inclusive carbon atoms, it being understood that for this description of the general formula (I), the term "substituted" concerning the groups as defined above: lower alkyl $R_a$—, lower alkenyl, A-(CH$_2$)$_m$—, phenyl-(CH$_2$)$_q$—, phenyl-(CH$_2$)$_q'$—, heteroaryl-(CH$_2$)$_q$—, means, when it is not specified, that these groups may be substituted by one or more radicals, which may be identical or different, and each one of which may represent independently of one another:
lower alkyl $R_c$—,
lower alkoxy $R_c$—O—,
lower acyl $R_c$—CO—,
trifluoromethyl,
carboxyl,
hydroxyl,
or halogen, where $R_c$ represents linear or branched alkyl having 1 to 6 inclusive carbon atoms, an optical isomer thereof, as well as, where appropriate, an addition salt thereof with a pharmaceutically-acceptable acid or base.

2. A compound according to claim 1 selected from those in which $R_5$ represents hydrogen, and an addition salt thereof with a pharmaceutically-acceptable base or acid.

3. A compound according to claim 1 selected from those in which X represents oxygen, and an addition salt thereof with a pharmaceutically-acceptable base or acid.

4. A compound according to claim 1 selected from those in which $R_5$ represents hydrogen and X represents oxygen, and an addition salt thereof with a pharmaceutically-acceptable base or acid.

5. A compound according to claim 1, selected, from those in which at least 1 of the 2 substituents $R_6$ and $R_7$ represents pyridinyl or a substituted pyridinyl, thereof, and an addition salt thereof with a pharmaceutically-acceptable base or acid.

6. A compound according to claim 1 selected from those in which at least 1 of the 2 substituents $R_6$ and $R_7$ represents quinolinyl or substituted quinolinyl, and an addition salt with a pharmaceutically-acceptable base or acid.

7. A compound according to claim 1 selected from those in which at least 1 of the 2 substituents $R_6$ and $R_7$ represents a phenyl group or a substituted phenyl group, and an addition salt thereof with a pharmaceutically-acceptable base or acid.

8. A compound according to claim 1 selected from N-Isobutyl-N-(4,6-dimethylpyridin-2-yl)-(6-hydroxy-3,4-dihydro-2,5,7,8-tetramethyl-2H[1]-benzopyran-2-yl)carboxamide, an optical isomer thereof, and an addition salt thereof with a pharmaceutically-acceptable base.

9. A compound according to claim 1 selected from N-(3,4,5-Trimethoxyphenyl)-(6-hydroxy-3,4-dihydro-2,5,7,8-tetramethyl-2H[1]-benzopyran-2-yl)carboxamide, an optical isomer thereof and an addition salt thereof with a pharmaceutically-acceptable base.

10. A compound according to claim 1 selected from N-(4-Methylquinolin-2-yl)-(6-hydroxy-3,4-dihydro- 2,5,7,8-tetramethyl-2H[1]-benzopyran-2-yl)carboxamide, an optical isomer thereof, and an addition salt thereof with a pharmaceutically-acceptable base.

11. A compound according to claim 1 which is selected from N-phenyl-(6-hydroxy-3,4-dihydro-2,5,7,8-tetramethyl-2H[1]-benzopyran-2-yl) carboxamide, an optical isomer thereof, and an addition salt thereof with a pharmaceutically-acceptable base.

12. A compound according to claim 1 which is N-phenyl-N-(buten-3-yl)-(6-hydroxy-3,4-dihydro-2,5,7,8-tetramethyl-2H[1]-benzopyran-2-yl) carboxamide.

13. A compound according to claim 1 which is N-cyclopropylmethyl-N-(4,6-dimethylpyridin-2-yl)-(6-hydroxy-3,4-dihydro-2,5,7,8-tetramethyl-2H[1]-benzopyran-2-yl) carboxamide.

14. A compound according to claim 1 which is N-(2,4,6-trimethylphenyl-(6-hydroxy-3,4-dihydro-2,5,7,8,-tetramethyl-2H[1]-benzopyran-2-yl) carboxamide.

15. A compound according to claim 1 which is N-(3,5-dichloro-4-hydroxphenyl)-(6-hydroxy-3,4-dihydro-2,5,7,8-tetramethyl-2H[1]-benzopyran-2-yl) carboxamide.

16. A compound according to claim 1 which is N-(2,4,5-trimethylphenyl)-(6-hydroxy-3,4-hydroxy-3,4-dihydro-2,5,7,8-tetramethyl-2H[1]-benzopyran-2-yl) carboxamide.

17. A compound according to claim 1 which is N-(2,6-dimethylphenyl)-(6-hydroxy-3,4-dihydro-2,5,7,8-tetramethyl-2H[1]-benzopyran-2-yl) carboxamide.

18. A compound according to claim 1 which is N-butyl-phenyl-(6-hydroxy-3,4-dihydro-2,5,7,8-tetramethyl-2H[1]-benzopyran-2-yl) carboxamide.

19. A compound according to claim 1 which is N-phenyl-(6-hydroxy-3,4-dihydro-2-methyl-7-tert-butyl-2H[1]-benzopyran-2-yl) carboxamide.

20. A pharmaceutical composition useful in treating or in preventing a disorder due to the phenomena of peroxidation and to eicosanoid biosynthesis comprising as active principle an effective peroxidation and eicosanoid biosynthesis-inhibitory amount of a compound as claimed in claim 1, in combination with a pharmaceutically-acceptable carrier or diluent.

21. A method of treating a living animal afflicted with a disorder due to the phenomena of peroxidation and to the disturbance of the eicosanoid biosynthesis comprising the step of administering to the said living animal an eicosanoid-biosynthesis and peroxidation-inhibitory amount of a compound as claimed in claim 1 which is effective for alleviation of said disorder.

* * * * *

UNITED STATES PATENT AND TRADEMARK OFFICE
CERTIFICATE OF CORRECTION

PATENT NO. : 5,315,017

DATED : May 24, 1994

INVENTOR(S) : Guillaume Le Baut, Jean Paul Babingui, Jacqueline Courant, Jean-Michel Robert, Pierre Renard, Daniel-Henri Caignard, Jean-Francois R. de la Faverie, Gerard Adam It is certified that error appears in the above-indentified patent and that said Letters Patent is hereby corrected as shown below:

Column 2, line 23; delete "$R_b$-", second occurrence, so that the complete group reads -- $R_a$-O-CO-$R_b$- --.
Column 2, approximately line 31; "E-$(CH_2)_q$ -d group" should read --E-$(CH_2)_q$- or a substituted group E-$(CH_2)_q$-d group --.
Column 4, line 59; "-O-$R_5$ of where" should read -- -O-$R_5$", where --.
Column 5, line 53; "hydrogen or" should read -- hydrogen atoms, or --.
Column 5, line 54; delete "atoms"
Column 9, line 4; "delete "2%".
Column 11, last line; "$\lambda$" should read -- $\nu$ --.
Column 12, line 35; "amine" should read -- amino --.
Column 12, line 45; "ine" should read -- ide --.
Column 12, line 67; "$\lambda$" should read -- $\nu$ --.
Column 13, line 20; "-2,5,7,7-" should read -- 2,5,7,8- --.
Column 14, approximately line 48; "2,4,7,8-" should read -- 2,5,7,8--.
Column 14, line 63; "1by" should read -- 1 by --.
Column 15, line 25; "C=H;" should read -- C=N --.
Column 16, approximately line 58; "11 N" should read -- 1, N --.
Column 23, line 8; "1)" should read -- [1] --.
Column 23, line 59; "Dihydro" should read --Dihydroxy--.
Column 24, approximately line 10; "2,4-" should read -- 2,2- --.
Column 24, line 50; "-2)carboxylic" should read -- -- -2-yl)carboxylic --.
Column 25, line 40; "C=N 1620: should read -- C=N: 1620 --.
Column 25, line 61; "19520" should read -- 1520 --.

UNITED STATES PATENT AND TRADEMARK OFFICE
CERTIFICATE OF CORRECTION

PATENT NO. : 5,315,017

DATED : May 24, 1994

INVENTOR(S) : Guillaume Le Baut, Jean Paul Babingui, Jacqueline Courant, Jean-Michel Robert, Pierre Renard, Daniel-Henri Caignard, Jean-Francois R. de la Faverie, Gerard Adam It is certified that error appears in the above-indentified patent and that said Letters Patent is hereby corrected as shown below:

Column 27, line 68; "-2H[1-" should read -- -2H[1]- --.
Column 28, line 49; "EXAMPLE130" should read
    -- EXAMPLE 130 --.
Column 29, approximately line 44; "-(6-" should read
    -- -[(6- --.
Column 31, line 55; "-2H[1)-" should read -- -2H[1] --.
Column 32, approximately line 23; "2H[19 " should read
    -- -2H[1] --.
Column 35, approximately line 13; "336.0" should read
    -- 3360 --.
Column 37, approximately lines 31 through 34; cancel most of
    these lines beginning with the word "form" in line 31 and
    ending with "8-yl, or" in line 34.
Column 38, line 1; "1 to 2" should read -- 1 or 2 --.
Column 38, line 12; ", means" should read -- , and means --.

Column 38, line 29; "f rom" should read -- from --.

Column 38, line 41; "selected, from should read
    -- selected from --.
Column 38, line 43; delete "thereof".

Signed and Sealed this

Fourth Day of October, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,315,017

DATED : May 24, 1994

INVENTOR(S) : Guillaume Le Baut, Jean-Paul Babingui, Jacqueline Courant, Jean-Michel Robert, Pierre Renard, Daniel-Henri Caignard, Jean-Francois R. de la Faverie and Gérard Adam It is certified that error appears in the above-indentified patent and that said Letters Patent is hereby corrected as shown below:

Title Page, Item [54]; and Col. 1. line 2, "BENZOPYRAN" should read
-- BENZOPYRAN COMPOUNDS --
Col. 39, line 18; "(2,4,6-trimethylphenyl-" should read
-- (2,4,6-trimethylphenyl)- --

Col. 39, line 26; delete "hydroxy-3,4-" (second occurrence)

Signed and Sealed this

Fourth Day of April, 1995

Attest:

BRUCE LEHMAN

*Attesting Officer*  *Commissioner of Patents and Trademarks*